(12) United States Patent
Bessant et al.

(10) Patent No.: US 12,426,641 B2
(45) Date of Patent: Sep. 30, 2025

(54) AEROSOL-GENERATING SYSTEM COMPRISING A HEALTH MONITORING DEVICE

(71) Applicant: Philip Morris Products S.A., Neuchatel (CH)

(72) Inventors: Michel Bessant, Neuchatel (CH); Simon Flury, Neuchatel (CH); Axel Teichert, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 967 days.

(21) Appl. No.: 17/419,111

(22) PCT Filed: Dec. 23, 2019

(86) PCT No.: PCT/EP2019/086905
§ 371 (c)(1),
(2) Date: Jun. 28, 2021

(87) PCT Pub. No.: WO2020/141128
PCT Pub. Date: Jul. 9, 2020

(65) Prior Publication Data
US 2022/0110372 A1    Apr. 14, 2022

(30) Foreign Application Priority Data

Dec. 31, 2018 (EP) .................... 18215954

(51) Int. Cl.
*A24F 47/00* (2020.01)
*A24F 40/20* (2020.01)
(Continued)

(52) U.S. Cl.
CPC .............. *A24F 40/53* (2020.01); *A24F 40/20* (2020.01); *A24F 40/51* (2020.01); *A24F 40/95* (2020.01)

(58) Field of Classification Search
CPC .......... A24F 40/50; A24F 40/51; A24F 40/53; A24F 40/60; A24F 40/65; A24F 40/90
See application file for complete search history.

(56) References Cited

U.S. PATENT DOCUMENTS 9,775,380 B2    10/2017  Fernando et al.
2007/0038330 A1  2/2007  Sullivan
(Continued)

FOREIGN PATENT DOCUMENTS

AU    2017260444 A1    12/2018
CN    102438470 A      5/2012
(Continued)

OTHER PUBLICATIONS

International Search Report and Written Opinion issued on Mar. 12, 2020 in PCT/EP2019/086905 filed on Dec. 23, 2019.
(Continued)

*Primary Examiner* — Eric Yaary
(74) *Attorney, Agent, or Firm* — Oblon, McClelland, Maier & Neustadt, L.L.P.

(57) ABSTRACT

An aerosol-generating system is provided, including: a health monitoring device including a sensor to collect health data from a user, a controller to receive the health data and determine a health parameter based on the data, and a health monitoring device power supply to supply electrical power to the controller and the sensor, the device not being an aerosol generator; an aerosol-generating device including a cavity to receive a plug of tobacco, an aerosol-generator to generate aerosol from the plug, and an aerosol-generating device power supply configured to supply electrical power to the aerosol-generator; and a charger including a cavity to receive the health monitoring and aerosol generating devices, and a charger power supply to transfer electrical power to the health monitoring device power supply, and
(Continued)

from the charging unit power supply to the aerosol-generating device power supply, the cavity being a single cavity.

11 Claims, 2 Drawing Sheets

(51) Int. Cl.

| | |
|---|---|
| *A24F 40/51* | (2020.01) |
| *A24F 40/53* | (2020.01) |
| *A24F 40/95* | (2020.01) |

(56) References Cited

U.S. PATENT DOCUMENTS

| | | | | |
|---|---|---|---|---|
| 2014/0378790 | A1 | 12/2014 | Cohen | |
| 2015/0004077 | A1 | 1/2015 | Wikswo et al. | |
| 2015/0327596 | A1 | 11/2015 | Alarcon et al. | |
| 2016/0137395 | A1 | 5/2016 | Fernando et al. | |
| 2017/0065002 | A1 | 3/2017 | Fernando et al. | |
| 2017/0089873 | A1 | 3/2017 | Neynavaee et al. | |
| 2017/0182267 | A1* | 6/2017 | Cameron | A61M 11/042 |
| 2017/0189629 | A1* | 7/2017 | Newberry | A61B 5/087 |
| 2017/0224020 | A1 | 8/2017 | Fernando et al. | |
| 2017/0238815 | A1 | 8/2017 | Luxon et al. | |
| 2017/0270260 | A1 | 9/2017 | Shetty et al. | |
| 2017/0360374 | A1 | 12/2017 | Elliott et al. | |
| 2018/0140009 | A1 | 5/2018 | Sur et al. | |
| 2018/0296777 | A1* | 10/2018 | Terry | A61M 11/042 |
| 2019/0175846 | A1 | 6/2019 | Terry et al. | |
| 2019/0254534 | A1 | 8/2019 | Koltowski et al. | |
| 2019/0364975 | A1 | 12/2019 | Fernando et al. | |
| 2020/0038603 | A1 | 2/2020 | Terry et al. | |

FOREIGN PATENT DOCUMENTS

| | | | |
|---|---|---|---|
| CN | 102665535 | A | 9/2012 |
| CN | 105377346 | A | 3/2016 |
| CN | 107820395 | A | 3/2018 |
| EP | 3 375 473 | A1 | 9/2018 |
| JP | 2006-516413 | A | 7/2006 |
| JP | 2018-507748 | A | 3/2018 |
| JP | 3218293 | U | 10/2018 |
| JP | 2018-536388 | A | 12/2018 |
| RU | 2014 132 075 | A | 2/2016 |
| RU | 2015 145 158 | A | 4/2017 |
| RU | 2016 146 694 | A | 5/2018 |
| WO | WO 03/020349 | A2 | 3/2003 |
| WO | WO 2016/090189 | A1 | 6/2016 |
| WO | WO 2016/096919 | A1 | 6/2016 |
| WO | WO 2017/192767 | A1 | 11/2017 |
| WO | WO2018/001910 | A1 | 1/2018 |
| WO | WO 2018/073343 | A2 | 4/2018 |
| WO | WO 2018/092097 | A1 | 5/2018 |
| WO | WO 2019/175810 | A1 | 9/2019 |

OTHER PUBLICATIONS

Rastogi et al., "Spontaneous ultraweak photon emission imaging of oxidative metabolic processes in human skin: effect of molecular oxygen and antioxidant defense system", Journal of Biomedical Optics, 2011, vol. 16, No. 9, 8 total pages, XP055599341.

Brancaleon et al., "Attenuated Total Reflection-Fourier Transform Infrared Spectroscopy as a Possible Method to Investigate Biophysical Parameters of Stratum Corneum In Vivo", The Journal of Investigative Dermatology, 2001, vol. 116, No. 3, pp. 380-386, XP055115433.

Ho et al., "Biological markers of oxidative stress: Applications to Cardiovascular research and practice", Redox Biology, 2013, vol. 1, No. 1, pp. 483-491, XP055472237.

Japanese Office Action issued Aug. 21, 2023 in Japanese Patent Application No. 2021-532937 (with English Translation), 8 pages.

Combined Chinese Office Action and Search Report issued Jan. 20, 2023 in Chinese Patent Application No. 201980081157.2 (with English Translation of Category of Cited Documents), 7 pages.

Combined Russian Office Action and Search Report issued Mar. 1, 2023 in Russian Patent Application No. 2021122132/14 (with English Translation), 21 pages.

Extended European Search Report issued on Oct. 11, 2019 in European Patent Application No. 18215954.1, 21 pages.

Partial European Search Report issued on Jul. 2, 2019 in European Patent Application No. 18215954.1, 24 pages.

* cited by examiner

AEROSOL-GENERATING SYSTEM COMPRISING A HEALTH MONITORING DEVICE

The present invention relates to an aerosol-generating system comprising a health monitoring device.

BACKGROUND

A number of electrically-operated aerosol-generating systems in which an aerosol-generating device having an electric heating element is used to heat an aerosol-forming substrate, such as a tobacco plug, have been proposed in the art. The aerosol-forming substrate may be provided as part of an aerosol-generating article which is inserted into a chamber or cavity in the aerosol-generating device. In some known systems, to heat the aerosol-forming substrate to a temperature at which it is capable of releasing volatile components that can form an aerosol, a heating element is inserted into or around the aerosol-forming substrate when the article is received in the aerosol-generating device.

Other known electrically-operated aerosol-generating systems are configured to heat a liquid aerosol-forming substrate, such as a nicotine-containing liquid. Such systems typically comprise a wick arranged to transport liquid aerosol-forming substrate from a storage portion and a heating element coiled around a portion of the wick.

One aim of such electrically-operated aerosol-generating systems is to reduce known harmful or potentially harmful smoke constituents of the type produced by the combustion and pyrolytic degradation of tobacco in conventional cigarettes.

BRIEF SUMMARY

The present inventors have recognised that it may be desirable for a user of an electrically-operated aerosol-generating system to monitor one or more health or fitness parameters to observe changes in such parameters, particularly when the user is transitioning from the use of conventional cigarettes to an electrically-operated aerosol-generating system.

It would be desirable to provide an aerosol-generating system that provides a user with a convenient way of monitoring one or more health or fitness parameters.

According to a first aspect of the present invention there is provided an aerosol-generating system comprising a health monitoring device, an aerosol-generating device and a charging unit. The health monitoring device comprises at least one sensor for collecting health data from a user and a controller arranged to receive the health data collected by the at least one sensor. The controller is configured to determine a health parameter based on the health data. The health monitoring device also comprises a health monitoring device power supply arranged to supply electrical power to at least one of the controller and the at least one sensor. The aerosol-generating device comprises an aerosol-generator for generating an aerosol from an aerosol-forming substrate and an aerosol-generating device power supply arranged to supply electrical power to the aerosol-generator. The charging unit comprises at least one cavity for receiving the health monitoring device and the aerosol generating device. The charging unit also comprises a charging unit power supply. The charging unit power supply is arranged to transfer electrical power from the charging unit power supply to the health monitoring device power supply when the health monitoring device is received within the at least one cavity. The charging unit power supply is arranged to transfer electrical power from the charging unit power supply to the aerosol-generating device power supply when the aerosol-generating device is received within the at least one cavity. The health monitoring device may not be an aerosol generator for generating an aerosol from an aerosol forming substrate.

Advantageously, the health monitoring device provides a user of the aerosol-generating system with a convenient way of monitoring one or more health or fitness parameters.

Advantageously, providing the aerosol-generating system with a charging unit configured to transfer electrical power to both of the health monitoring device and the aerosol-generating device provides a user of the aerosol-generating system with a convenient way of charging both the health monitoring device and the aerosol-generating device.

Advantageously, the charging unit may facilitate the use of a relatively small health monitoring device power supply. Advantageously, a small health monitoring device power supply may facilitate providing a health monitoring device have at least one of a desired size and a desired shape.

Advantageously, the charging unit may protect the health monitoring device from damage when the health monitoring device is not be used to collect health data using the at least one sensor.

The charging unit power supply may be a DC voltage source. In preferred embodiments, the charging unit power supply is a battery. For example, the charging unit power supply may be a nickel-metal hydride battery, a nickel cadmium battery, or a lithium based battery, for example a lithium-cobalt, a lithium-iron-phosphate or a lithium-polymer battery. The charging unit power supply may alternatively be another form of charge storage device such as a capacitor. The charging unit power supply may be rechargeable.

Preferably, the health monitoring device comprises at least one health monitoring device electrical contact and the charging unit comprises at least one charging unit electrical contact. Preferably, the at least one charging unit electrical contact is arranged to contact the at least one health monitoring device electrical contact when the health monitoring device is received within the at least one cavity. Preferably, the charging unit is arranged to transfer electrical power from the charging unit power supply to the health monitoring device power supply via the at least one charging unit electrical contact and the at least one health monitoring device electrical contact. The at least one health monitoring device electrical contact may comprise a first magnetic material and the at least one charging unit electrical contact may comprise a second magnetic material such that, when the health monitoring device is charging, a magnetic connection between the at least one health monitoring device electrical contact and the at least one charging unit electrical contact acts to retain the health monitoring device in the charging unit.

Preferably, the aerosol-generating device comprises at least one aerosol-generating device electrical contact and the charging unit comprises at least one charging unit electrical contact. Preferably, the at least one charging unit electrical contact is arranged to contact the at least one aerosol-generating device electrical contact when the aerosol-generating device is received within the at least one cavity. Preferably, the charging unit is arranged to transfer electrical power from the charging unit power supply to the aerosol-generating device power supply via the at least one charging unit electrical contact and the at least one aerosol-generating device electrical contact. The at least one aerosol-generating device electrical contact may comprise a first magnetic material and the at least one charging unit electrical contact may comprise a second magnetic material such that, when the aerosol-generating device is charging, a magnetic connection between the at least one aerosol-generating device electrical contact and the at least one charging unit electrical contact acts to retain the aerosol-generating device in the charging unit.

The aerosol generating device may comprise a device cavity arranged to receive a plug of tobacco.

Preferably, the charging unit comprises a charging unit controller arranged to control the transfer of electrical power from the charging unit power supply to each of the health monitoring device power supply and the aerosol-generating device power supply when the health monitoring device and the aerosol-generating device respectively are received within the at least one cavity.

The at least one cavity may be arranged to receive the health monitoring device and the aerosol-generating device simultaneously or separately.

The at least one cavity of the charging unit may be a single cavity. The single cavity may be arranged to receive each of the health monitoring device and an aerosol-generating device. The single cavity may be sized to simultaneously receive the health monitoring device and an aerosol-generating device. The single cavity may be sized to receive only one of the health monitoring device and an aerosol-generating device at a time. In other words, the single cavity may be sized to separately receive each of the health monitoring device and the aerosol-generating device.

The at least one cavity may comprise a first cavity arranged to receive the health monitoring device and a second cavity arranged to receive an aerosol-generating device. In embodiments in which the charging unit comprises at least one charging unit electrical contact, preferably the at least one charging unit electrical contact comprises at least one first charging unit electrical contact arranged to contact the at least one health monitoring device electrical contact when the health monitoring device is received within the first cavity and at least one second charging unit electrical contact arranged to contact the at least one aerosol-generating device electrical contact when an aerosol-generating device is received within the second cavity.

Preferably, the health monitoring device comprises a feedback device. Advantageously, the feedback device may prompt a user to take a particular action when using the health monitoring device. Advantageously, the feedback device may indicate to the user when a particular action has been completed. The at least one sensor may comprise a plurality of sensors and the feedback device may indicate which sensor is activated. The feedback device may give a user an indication of the data generated by a sensor; in other words, the feedback device may give a user an indication of the result of a sensing measurement by a sensor. Exemplary uses of the feedback device are described herein. The feedback device may comprise at least one of an audio device, a visual device, and a tactile device. The audio device may comprise a speaker. The visual device may comprise at least one light emitting diode. The visual device may comprise a visual display, for example a liquid crystal display. The tactile device may comprise a vibration motor.

The feedback device may comprise a user input means by which a user may provide information to the health monitoring device, or control the health monitoring device. The user input means may comprise at least one of a button, switch, touch sensor, or dial. The user input means may allow a user to activate or deactivate the health monitoring device. The at least one sensor may comprise a plurality of sensors and the user input means may allow a user to select which of sensors is activated. This is advantageous where it is not possible for more than one of the plurality of sensors to be activated at one time. The user input means may allow a user to determine the charge status of the health monitoring device power supply.

The at least one sensor of the health monitoring device may comprise at least one of an air flow sensor, an air pressure sensor, an audio sensor, and an electrochemical gas sensor. The controller may be configured to determine a respiratory parameter based on sensor data received by the controller from the at least one sensor.

The respiratory parameter may comprise at least one of a spirometry parameter and a breath gas level. The respiratory parameter may comprise the respiration capacity of the user.

Advantageously, a spirometry parameter may facilitate determining or monitoring changes in lung function. Determining or monitoring changes in lung function may be particularly advantageous for a user transitioning away from the use of conventional cigarettes.

Advantageously, determining a breath gas level for one or more gases may allow a user to compare breath gas levels after using different aerosol-generating devices or articles, including conventional cigarettes.

The spirometry parameter may comprise at least one of total volume, volumetric flow rate, flow speed, and peak flow.

In embodiments in which the controller is configured to determine a spirometry parameter based on the sensor data, preferably the at least one sensor comprises at least one of an air flow sensor, an air pressure sensor, and an audio sensor. The at least one sensor may comprise at least two of an air flow sensor, an air pressure sensor, and an audio sensor. The at least one sensor may comprise a combined air sensor that functions as at least two of an air flow sensor, an air pressure sensor, and an audio sensor.

The air flow sensor may comprise at least one of a rotary sensor, a hot wire sensor, a cold wire sensor, an ultrasonic sensor, an acoustic resonance sensor, and a microelectromechanical systems sensor (for example, a thermal membrane sensor).

The air pressure sensor may comprise at least one of a hot wire sensor, a cold wire sensor, a piezoresistive sensor, a capacitive sensor, a Hall effect sensor, and a piezoelectric sensor.

The audio sensor may comprise at least one of a piezoelectric transducer and a microelectromechanical systems microphone. The controller may be arranged to receive data from the audio sensor and determine whether a user has coughed. The controller may count the number of coughs a user makes in a given period.

In embodiments in which the health monitoring device comprises a feedback device, the feedback device may be arranged to provide user feedback during determination of a spirometry parameter. The feedback device may be arranged to provide user feedback to indicate when a user should begin exhaling into the health monitoring device. The feedback device may be arranged to provide user feedback to indicate when a user may cease exhaling into the health monitoring device.

The breath gas level may comprise at least one of a breath carbon monoxide level and a breath nitrogen dioxide level.

In embodiments in which the controller is configured to determine a breath gas level based on the sensor data, preferably the at least one sensor comprises an electrochemical gas sensor. The electrochemical gas sensor may comprise a semiconductor gas sensor. The semiconductor gas sensor may be a metal-oxide gas sensor. The semiconductor gas sensor may be a N-type semiconductor gas sensor, such as a tin-oxide gas sensor. N-type semiconductor sensors decrease in electrical resistance in the presence of a reducing gas, such as carbon monoxide or ammonia, and increase in electrical resistance in the presence of oxidizing gas, such as oxygen, nitric oxide, or nitrogen dioxide. The semiconductor gas sensor may be is a P-type semiconductor gas sensor. P-type semiconductor gas sensors behave in the opposite manner, so they increase in electrical resistance in the presence of a reducing gas and decrease in electrical resistance in the presence of oxidizing gas.

The at least one sensor may comprise a plurality of electrochemical gas sensors. Preferably, at least two of the electrochemical gas sensors may be configured to be sensitive to different gases. One electrochemical gas sensor may be configured to detect reducing gases and another may be configured to detect oxidising gases. Both electrochemical gas sensors may be sensitive to reducing gases but may be differently tuned (for example, by changing the composition, fabrication or doping of a gas sensing layer) to be particularly sensitive to different gases. For example, the plurality of electrochemical gas sensors may comprise a first electrochemical gas sensor tuned to sense carbon monoxide and a second electrochemical gas sensor tuned to sense nitrogen dioxide.

In embodiments in which the health monitoring device comprises a feedback device, the feedback device may be arranged to provide user feedback during determination of a breath gas level. The feedback device may be arranged to provide user feedback to indicate when a user should begin exhaling into the health monitoring device. The feedback device may be arranged to provide user feedback to indicate when a user may cease exhaling into the health monitoring device.

The at least one sensor of the health monitoring device may comprise at least one of an electrode, an optical sensor, and a pressure sensor. The controller may be configured to determine a cardiopulmonary parameter based on sensor data received by the controller from the at least one sensor.

The at least one sensor may comprise an optical sensor. The controller may be configured to determine at least one of a heart rate, a heart rate variability, an oxygen saturation level, a carbon monoxide saturation level, and an oxidative stress level, based on the sensor data generated by the optical sensor.

The optical sensor may comprise a multiple spatially resolved reflection spectroscopy sensor. The controller may be configured to determine an oxidative stress level based on the sensor data generated by the multiple spatially resolved reflection spectroscopy sensor. The multiple spatially resolved reflection spectroscopy sensor may be suited to determining an oxidative stress level when the multiple spatially resolved reflection spectroscopy sensor is pressed against the palm of a user's hand. A suitable multiple spatially resolved reflection spectroscopy sensor is produced by Biozoom Services GmbH.

In embodiments in which the health monitoring device comprises a feedback device, the feedback device may be arranged to provide user feedback during determination of an oxidative stress level. The feedback device may be arranged to provide user feedback to indicate when a user should press the multiple spatially resolved reflection spectroscopy sensor against the palm of their hand. The feedback device may be arranged to provide user feedback to indicate when a user may cease pressing the multiple spatially resolved reflection spectroscopy sensor against the palm of their hand.

The optical sensor may comprise at least one light emitting diode and at least one photodiode, wherein the controller is configured to determine at least one of a heart rate, a heart rate variability, an oxygen saturation level, and a carbon monoxide saturation level, based on the sensor data generated by the at least one photodiode. The at least one light emitting diode and the at least one photodiode may function together as a pulse oximeter.

The at least one sensor may comprise an optical sensor and a pressure sensor, wherein the controller is configured to determine a blood pressure based on the sensor data generated by the optical sensor and the pressure sensor. A suitable arrangement for determining blood pressure based on data from an optical sensor and a pressure sensor is described in WO-2016/096919-A1. The optical sensor may be a photoplethysmographic sensor. The optical sensor and the pressure sensor may be particularly suited to determining a blood pressure when the optical sensor and the pressure sensor are pressed against a user's fingertip.

To facilitate determination of a blood pressure based on data from the optical sensor and the pressure sensor, it may be necessary for a user to press a fingertip against the optical sensor and the pressure sensor at a constant and predetermined pressure. In embodiments in which the health monitoring device comprises a feedback device, the feedback device may be arranged to provide user feedback during determination of a blood pressure to indicate when a user is pressing a fingertip against the optical sensor and the pressure sensor with a predetermined pressure.

The health monitoring device may comprise a motion sensor positioned inside the housing, wherein the controller is arranged to receive motion sensor data generated by the motion sensor, and wherein the controller is configured to determine a motion parameter based on the motion sensor data. Preferably, the motion parameter comprises data relating to movement by a user holding or carrying the health monitoring device. The motion parameter may be a number of walking steps made by a user. The motion parameter may be a number of running strides made by a user.

The motion sensor may be configured to generate motion sensor data when the health monitoring device is not received within the at least one cavity of the charging unit. The motion sensor may be configured to generate motion sensor data when the health monitoring device is received within the at least one cavity of the charging unit. The motion sensor may be configured to generate motion sensor data regardless of whether the health monitoring device is received within the at least one cavity of the charging unit.

Preferably, the motion sensor comprises at least one of an accelerometer and a gyroscope. Preferably, the motion sensor is an inertial measurement unit comprising at least one accelerometer and at least one gyroscope. Advantageously, an inertial measurement unit facilitates measurement of both linear acceleration and rotational acceleration. Preferably, the inertial measurement unit comprises at least three accelerometers arranged to sense linear acceleration along three orthogonal axes. Preferably, the inertial measurement unit comprises at least three gyroscopes arranged to sense rotational acceleration around three orthogonal axes.

Preferably, the health monitoring device comprises a memory unit arranged to store at least one of sensor data generated by the at least one sensor and one or more parameters determined by the controller. In embodiments in which the health monitoring device comprises a motion sensor, the memory unit may be arranged to store motion sensor data.

Preferably, the health monitoring device comprises a communication unit. The communication unit may be arranged to receive data from at least one external device. The communication unit may be arranged to transmit data to at least one external device. External devices may include at least one of the charging unit, the aerosol-generating device, a smartphone, a tablet computer, a personal computer, and a laptop.

Advantageously, transmitting data from the health monitoring system to an external device may facilitate use of the data by a user of the health monitoring system. For example, transmitting one or more parameters determined by the controller of the health monitoring system to a smartphone or a personal computer may facilitate a graphical display of the one or more parameters. Advantageously, graphically displaying the one or more parameters determined by the controller may facilitate the observation of changes in the one or more parameters over a period of time.

In embodiments in which the health monitoring device comprises a memory unit, the controller may be arranged to transmit data from the memory unit via the communication unit.

The communication unit may comprise a wireless communication unit. In other words, the communication unit may be arranged to communicate wirelessly with an external device. Advantageously, wireless communication may be more convenient than wired communication. The wireless communication unit may be arranged to communicate using at least one wireless protocol. Suitable wireless protocols include Wi-Fi, Bluetooth®, ultra-wideband, near-field communication, and Zigbee.

The communication unit may comprise a wireless communication unit. In other words, the communication unit may be arranged to communicate wirelessly with an external device. Advantageously, wireless communication may be more convenient than wired communication. The wireless communication unit may be arranged to communicate using at least one wireless protocol. Suitable wireless protocols include Wi-Fi, Bluetooth, ultra-wideband, near-field communication, and Zigbee.

Where present, the health monitoring device power supply may be arranged to supply electrical power to at least one of the motion sensor, the memory unit, and the communication unit.

The health monitoring device power supply may be a DC voltage source. In preferred embodiments, the health monitoring device power supply is a battery. For example, the health monitoring device power supply may be a nickel-metal hydride battery, a nickel cadmium battery, or a lithium based battery, for example a lithium-cobalt, a lithium-iron-phosphate or a lithium-polymer battery. The health monitoring device power supply may alternatively be another form of charge storage device such as a capacitor. The health monitoring device power supply may be rechargeable. Preferably, the health monitoring device power supply has a capacity of between about 50 milliamp hours and about 200 milliamp hours, more preferably between about 50 milliamp hours and about 150 milliamp hours, more preferably between about 50 milliamp hours and about 100 milliamp hours. The health monitoring device power supply may have a capacity of between about 50 milliamp hours and about 60 milliamp hours.

The health monitoring device may comprise a housing.

In embodiments in which the at least one sensor comprises at least one of an air flow sensor, an air pressure sensor, an audio sensor, and an electrochemical gas sensor for determining a respiratory parameter, the housing may define a cavity, wherein the one or more sensors may be in fluid communication with the cavity. The one or more sensors may be positioned within the cavity. Preferably, the housing defines an air inlet in fluid communication with the cavity and an air outlet in fluid communication with the cavity. Advantageously, a user may exhale into the air inlet to force air from the user's mouth and lungs through the cavity via the air inlet and the air outlet. Advantageously, the one or more sensors is in fluid communication with the air flow through the cavity. Advantageously, the air inlet, the cavity, and the air outlet can be formed with predetermined dimensions during manufacture of the housing. Advantageously, the predetermined dimensions of the air inlet, the cavity and the air outlet may be used to calibrate the one or more sensors. In other words, the controller may be configured to determine the respiratory parameter based on the sensor data and the predetermined dimensions of the air inlet, the cavity and the air outlet.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the health monitoring device comprises a mouthpiece. The air inlet may form part of the mouthpiece. The mouthpiece may define a mouthpiece air inlet in fluid communication with the air inlet defined by the housing.

The mouthpiece may be formed integrally with the housing.

The mouthpiece may be formed separately from the housing. The mouthpiece may be attached to the housing. The mouthpiece may be removably attachable to the housing. The provision of a removable mouthpiece may advantageously improve the hygiene and cleanliness of using the health monitoring device. The mouthpiece may be disposable. Where the mouthpiece is disposable, it may be designed to be replaced each time the mouthpiece is used. Where the mouthpiece is disposable, it may be designed to be replaced at regular intervals of time or usage. For example, the disposable mouthpiece may be designed to be replaced every month or every ten uses of the mouthpiece. The mouthpiece may comprise a filtration component to retail particles from as user's breath. This may advantageously prevent such particles coming into contact with the at least one sensor and may thereby reduce the need to clean the at least one sensor or other parts of the health monitoring device.

Preferably, the health monitoring device is portable. The health monitoring device may have an elongate shape. The health monitoring device may have a size comparable to the aerosol-generating device, or a conventional cigar or cigarette. The health monitoring device may have a shape comparable to the aerosol-generating device, or a conventional cigar or cigarette. The health monitoring device may have a total length between about 30 millimetres and about 150 millimetres. The health monitoring device may have an external diameter between about 5 millimetres and about 30 millimetres.

The aerosol-generating device may comprise an aerosol-forming substrate. The aerosol-generating device may comprise a storage portion and an aerosol-forming substrate positioned within the storage portion. The aerosol-forming substrate may be a liquid aerosol-forming substrate. The liquid aerosol-forming substrate may comprise nicotine. The liquid aerosol-forming substrate may comprise at least one of water and an aerosol former. Suitable aerosol formers include glycerin and propylene glycol. The aerosol-generator may comprise a heating element. The heating element may comprise a resistive heating element. The heating element may comprise an inductor. The aerosol-generating device may comprise a transfer element arranged to transfer liquid aerosol-forming substrate from the storage portion to the heating element. The transfer element may comprise a capillary wick.

The aerosol-generating device may be arranged to receive an aerosol-forming substrate. The aerosol-generating device may comprise a device cavity arranged to receive an article comprising an aerosol-forming substrate or a cartridge comprising an aerosol-forming substrate. The aerosol-generator may comprise a heating element. The heating element may comprise a resistive heating element. The heating element may comprise an inductor. The heating element may be arranged to heat a solid aerosol-forming substrate. The solid aerosol-forming substrate may comprise tobacco. The solid aerosol-forming substrate may comprise a plug of tobacco. The heating element may be arranged for insertion into the solid aerosol-forming substrate when the solid aerosol-forming substrate is received within the aerosol-generating device.

According to a second aspect of the present invention, there is provided a health monitoring device according to the first aspect of the present invention in accordance with any of the embodiments described herein.

The present inventors have recognised that it may be desirable for a user of an electrically-operated aerosol-generating system to monitor one or more health or fitness parameters to observe changes in such parameters, particularly when the user is transitioning from the use of conventional cigarettes to an electrically-operated aerosol-generating system. However, known fitness trackers typically allow measurement of a limited range of parameters, such as heart rate, number of steps, and so forth. Therefore, known fitness trackers are of limited use in monitoring health or fitness changes in a user transitioning away from the use of conventional cigarettes.

It would be desirable to provide a device for monitoring health or fitness parameters that offers improved or increased functionality compared to known fitness trackers.

According to a third aspect of the present invention there is provided a health monitoring device comprising a first sensor, a second sensor, and a controller. The first sensor comprises at least one of an air flow sensor, an air pressure sensor, an audio sensor, and an electrochemical gas sensor. The second sensor comprises at least one of an electrode, an optical sensor, and a pressure sensor. The controller is arranged to receive first sensor data generated by the first sensor and second sensor data generated by the second sensor. The controller is configured to determine a respiratory parameter based on the first sensor data. The controller is configured to determine a cardiopulmonary parameter based on the second sensor data.

Advantageously, a health monitoring device according to the third aspect of the present invention facilitates monitoring of a respiratory parameter and a cardiopulmonary parameter. Advantageously, a health monitoring device according to the third aspect of the present invention provides improved functionality compared to known fitness trackers, which allow monitoring of a cardiopulmonary parameter only. Advantageously, the improved functionality of a health monitoring device according to the third aspect of the present invention may be particularly useful for a user transitioning away the use of conventional cigarettes.

Preferably, the health monitoring device comprises a health monitoring device power supply arranged to supply electrical power to at least one of the first sensor, the second sensor, and the controller.

The health monitoring device according to the third aspect of the present invention may comprise any of the preferred or optional features described herein with respect to the first aspect of the present invention.

According to a fourth aspect of the present invention there is provided a health monitoring system comprising a charging unit and a health monitoring device according to the third aspect of the present invention in accordance with any of the embodiments described herein in which the health monitoring device comprises a health monitoring device power supply. The charging unit comprising at least one cavity for receiving the health monitoring device and a charging unit power supply. The charging unit power supply is arranged to transfer electrical power from the charging unit power supply to the health monitoring device power supply when the health monitoring device is received within the at least one cavity.

The charging unit may comprise any of the preferred or optional features described herein with respect to the first aspect of the present invention.

According to a fifth aspect of the present invention there is provided an aerosol-generating system comprising an aerosol-generating device and an aerosol-generating system according to the fourth aspect of the present invention in accordance with any of the embodiments described herein. The aerosol-generating device comprises an aerosol-generating for generating an aerosol from an aerosol-forming substrate and an aerosol-generating device power supply arranged to supply electrical power to the aerosol-generator. The at least one cavity of the charging unit is arranged to receive the aerosol-generating device. The charging unit power supply is arranged to transfer electrical power from the charging unit power supply to the aerosol-generating device power supply when the aerosol-generating device is received within the at least one cavity.

The aerosol-generating device may comprise any of the preferred or optional features described herein with respect to the first aspect of the present invention.

BRIEF DESCRIPTION OF THE DRAWINGS

The invention will now be further described, by way of example only, with reference to the accompanying drawings in which.

DETAILED DESCRIPTION

Figure 1:
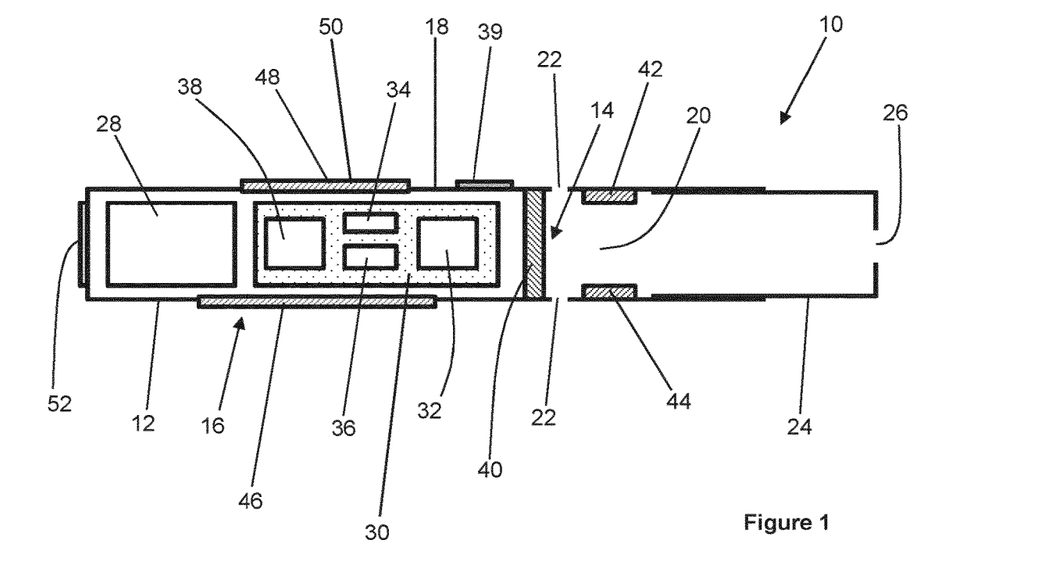
FIG. 1 shows a cross-sectional view of a health monitoring device according to an embodiment of the present invention.

FIG. 1 shows a cross-sectional view of a health monitoring device 10 according to an embodiment of the present invention. The health monitoring device 10 comprises a housing 12, a plurality of first sensors 14 positioned inside the housing 12 and a plurality of second sensors 16 positioned on an external surface 18 of the housing 12. The housing 12 defines a cavity 20 in which the plurality of first sensors 14 is positioned and a plurality of air outlets 22 in fluid communication with a downstream end of the cavity 20. A mouthpiece 24 is removably attached to an upstream end of the housing 12 and defines an air inlet 26 in fluid communication with an upstream end of the cavity 20.

Positioned within a downstream end of the housing 12 is a health monitoring device power supply 28 comprising a rechargeable battery and a control electronics board 30. Positioned on the control electronics boards 30 are a controller 32, a memory unit 34, a wireless communication unit 36, and a motion sensor 38. The wireless communication unit 36 is configured for wireless communication using a Bluetooth® protocol. The motion sensor 38 is an inertial measurement unit comprising a plurality of accelerometers and gyroscopes. The controller 32 is configured to determine at least one motion parameter based on sensor data from the motion sensor 38. The controller 32 is configured to store the determined motion parameters on the memory unit 34. The controller 32 is configured to transmit the determined motion parameters to one or more external devices using the wireless communication unit 36.

The health monitoring device 10 also comprises a feedback device 39 comprising at least one light emitting diode integrated with a push button. The controller 32 can provide feedback to a user in the form of visual signals using the at least one light emitting diode of the feedback device 39. The push button allows a user to interact with the health monitoring device 10. For example, pushing the push button may provide a signal to the controller 32 to begin receiving sensor data from at least one of the plurality of first sensors 14, the plurality of second sensors 16, and the motion sensor 38.

The plurality of first sensors 14 comprises an electrochemical gas sensor 40, a combined air pressure and air flow sensor 42, and an audio sensor 44. The controller 32 is configured to determine a plurality of respiratory parameters based on first sensor data from the plurality of first sensors 14 when a user exhales into the cavity 20 through the air inlet 26. The controller 32 is configured to determine a spirometry parameter based on sensor data from at least one of the audio sensor 44 and the combined air pressure and air flow sensor 42. The controller 32 is configured to determine a carbon monoxide breath gas level based on sensor data from the electrochemical gas sensor 40. The controller 32 is configured to store the determined respiratory parameters on the memory unit 34. The controller 32 is configured to transmit the determined respiratory parameters to one or more external devices using the wireless communication unit 36.

The plurality of second sensors 16 comprises a first optical sensor 46 and a combination sensor comprising a second optical sensor 48 and pressure sensor 50. The first optical sensor 46 is a multiple spatially resolved reflection spectroscopy sensor and the second optical sensor 48 is a pulse oximeter. The controller 32 is configured to determine a plurality of cardiopulmonary parameters based on second sensor data from the plurality of second sensors 16 when a user presses their skin against at least one of the plurality of second sensors 16.

The controller 32 is configured to determine an oxidative stress level based on sensor data from the first optical sensor 46 when a user holds the palm of their hand against the first optical sensor 46.

The controller 32 is configured to determine a heart rate and an oxygen saturation level based on sensor data from the second optical sensor 48 when a user holds a fingertip against the second optical sensor 48. Based on sensor data from the pressure sensor 50, the controller 32 is configured to determine the pressure applied to the pressure sensor 50 and the second optical sensor 48 by a user's fingertip. When the pressure applied to by a user is within a predetermined range, the controller 32 may provide a visual indication to a user via the feedback device 39. When a user is pressing a fingertip against the pressure sensor 50 and the second optical sensor 48 at a pressure within the predetermined range, the controller 32 is configured to determine a blood pressure based on sensor data from the second optical sensor 48.

The controller 32 is configured to store the determined cardiopulmonary parameters on the memory unit 34. The controller 32 is configured to transmit the determined cardiopulmonary parameters to one or more external devices using the wireless communication unit 36.

The health monitoring device 10 also comprises at least one health monitoring device electrical contact 52. The health monitoring device 10 is arranged to receive electrical power from an external device via the at least one health monitoring device electrical contact 52 for recharging the health monitoring device power supply 28.

Figure 2:
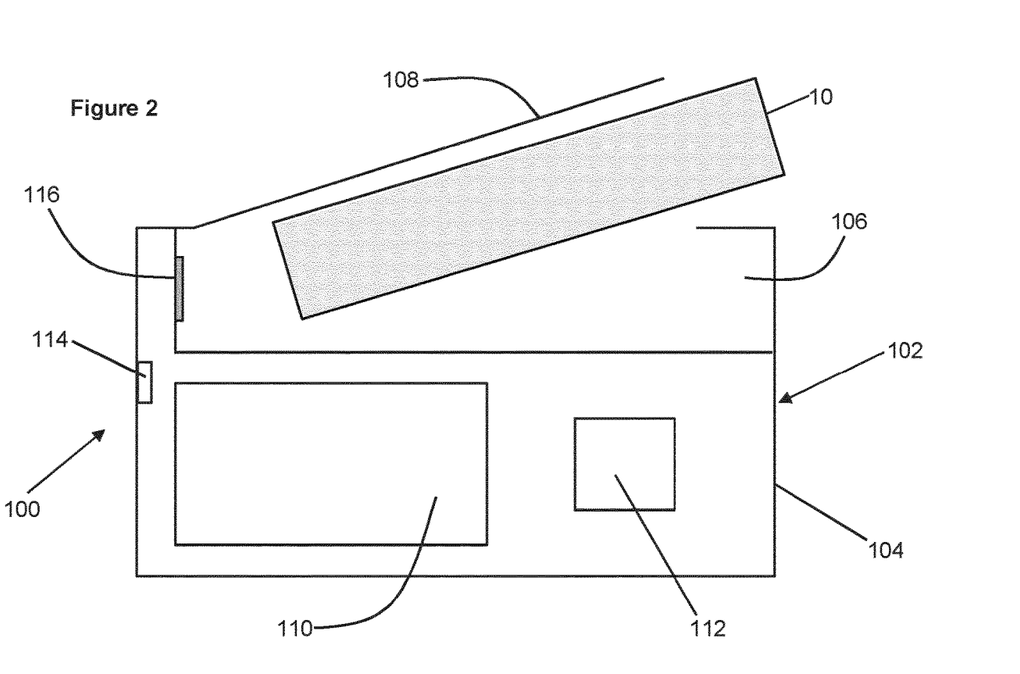
FIG. 2 shows a cross-sectional view of a charging unit and the health monitoring device of FIG. 1.

FIG. 2 shows a cross-sectional view of a health monitoring system 100 according to a first embodiment of the present invention and comprising the health monitoring device 10 of FIG. 1. The health monitoring system 100 also comprises charging unit 102 comprising a charging unit housing 104 defining a cavity 106 for receiving the health monitoring device 10. The charging unit housing 104 comprises a hinged portion 108 that may be opened to allow insertion of the health monitoring device 10 into the cavity 106 and removal of the health monitoring device 10 from the cavity 106. The hinged portion 108 may be closed to contain the health monitoring device 10 within the cavity 106.

Positioned within the charging unit housing 104 is a charging unit power supply 110 and a charging unit controller 112. The charging unit power supply 110 comprises a rechargeable battery. The charging unit 102 also comprises a micro-USB connector 114 for connection to an external power supply for recharging the charging unit power supply 110.

The charging unit 102 also comprises at least one charging unit electrical contact 116 positioned within the cavity 106 to engage the at least one health monitoring device electrical contact 52 when the health monitoring device 10 is received within the cavity 106. The charging unit controller 112 is configured to supply electrical power from the charging unit power supply 110 to the health monitoring device power supply 28 via the at least one charging unit electrical contact 116 and the at least one health monitoring device electrical contact 52 to recharge the health monitoring device power supply 28.

Figure 3:
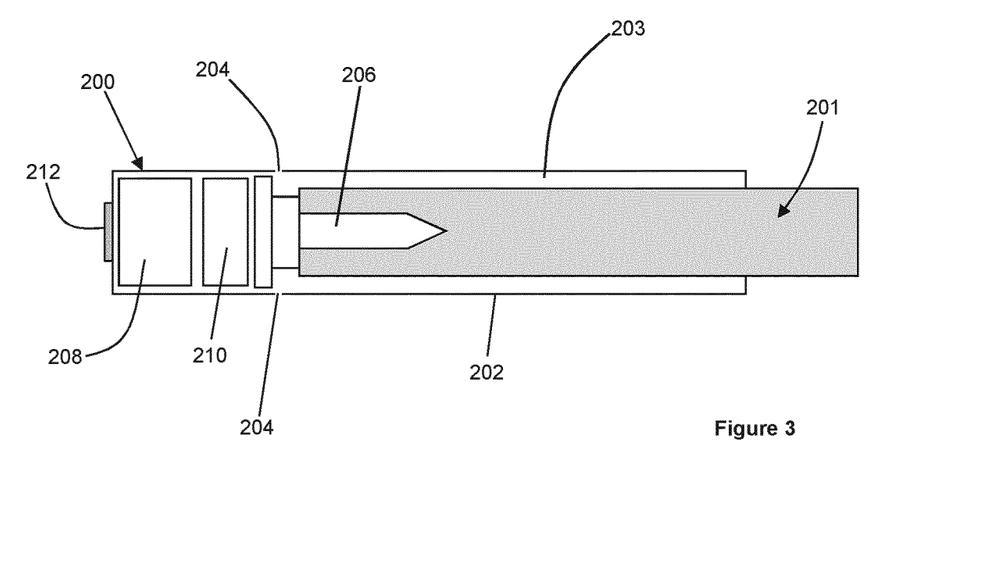
FIG. 3 shows a cross-sectional view of an aerosol-generating device in combination with an aerosol-generating article.

FIG. 3 shows a cross-sectional view of an aerosol-generating device 200 in combination with an aerosol-generating article 201. The aerosol-generating device 200 comprises a housing 202 defining a cavity 203 for receiving the aerosol-generating article 201, as shown in FIG. 3. The housing 202 also defines a plurality of air inlets 204 in fluid communication with an upstream end of the cavity 203. An electric heater 206 is positioned within the cavity 203 and arranged for insertion into the aerosol-generating article 201 when the aerosol-generating article 201 is received within the cavity 203. The aerosol-generating device 200 also comprises an aerosol-generating device power supply 208, an aerosol-generating device controller 210, and at least one aerosol-generating device electrical contact 212. During use, the aerosol-generating device controller 210 controls a supply of electrical power from the aerosol-generating device power supply 208 to the electric heater 206 for heating the aerosol-generating article 201.

The aerosol-generating device power supply 208 comprises a rechargeable battery. The aerosol-generating device 200 is arranged to receive electrical power from an external device via the at least one aerosol-generating device electrical contact 212 for recharging the aerosol-generating device power supply 208. The aerosol-generating device 200 may be combined with the health monitoring system 100 of FIG. 2 to form an aerosol-generating system in which the aerosol-generating device 200 may be received within the cavity 106 of the charging unit 102 when the health monitoring device 10 is removed from the cavity 106. The charging unit controller 112 is configured to supply electrical power from the charging unit power supply 110 to the aerosol-generating device power supply 208 via the at least one charging unit electrical contact 116 and the at least one aerosol-generating device electrical contact 212 to recharge the aerosol-generating device power supply 208.

Figure 4:
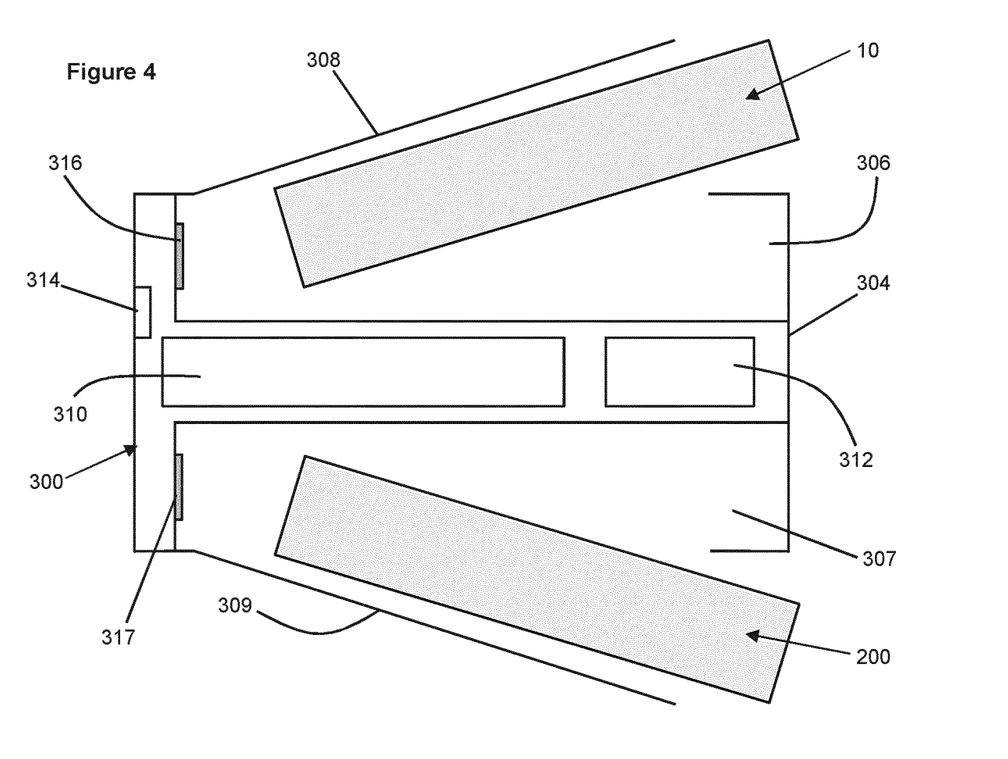
FIG. 4 shows a cross-sectional view of an aerosol-generating system comprising the health monitoring device of FIG. 1, the charging unit of FIG. 2 and the aerosol-generating device of FIG. 3.

Alternatively, according to a second embodiment of the present invention shown in FIG. 4, the aerosol-generating system may comprise a charging unit 300 configured to receive simultaneously the health monitoring device 10 and the aerosol-generating device 200. The charging unit 300 comprises a charging unit housing 304 defining a first cavity 306 for receiving the health monitoring device 10 and a second cavity 307 for receiving the aerosol-generating device 200.

The charging unit housing 304 comprises a first hinged portion 308 that may be opened to allow insertion of the health monitoring device 10 into the first cavity 306 and removal of the health monitoring device 10 from the first cavity 306. The first hinged portion 308 may be closed to contain the health monitoring device 10 within the first cavity 306.

The charging unit housing 304 comprises a second hinged portion 309 that may be opened to allow insertion of the aerosol-generating device 200 into the second cavity 307 and removal of the aerosol-generating device 200 from the second cavity 307. The second hinged portion 309 may be closed to contain the aerosol-generating device 200 within the second cavity 307.

Positioned within the charging unit housing 304 is a charging unit power supply 310 and a charging unit controller 312. The charging unit power supply 310 comprises a rechargeable battery. The charging unit 300 also comprises a micro-USB connector 314 for connection to an external power supply for recharging the charging unit power supply 310.

The charging unit 300 also comprises at least one first charging unit electrical contact 316 positioned within the first cavity 306 to engage the at least one health monitoring device electrical contact 52 when the health monitoring device 10 is received within the first cavity 306. The charging unit controller 312 is configured to supply electrical power from the charging unit power supply 310 to the health monitoring device power supply 28 via the at least one first charging unit electrical contact 316 and the at least one health monitoring device electrical contact 52 to recharge the health monitoring device power supply 28.

The charging unit 300 also comprises at least one second charging unit electrical contact 317 positioned within the second cavity 307 to engage the at least one aerosol-generating device electrical contact 212 when the aerosol-generating device 200 is received within the second cavity 307. The charging unit controller 312 is configured to supply electrical power from the charging unit power supply 310 to the aerosol-generating device power supply 208 via the at least one second charging unit electrical contact 317 and the at least one aerosol-generating device electrical contact 212 to recharge the aerosol-generating device power supply 208.

The invention claimed is:

1. An aerosol-generating system, comprising:
 a health monitoring device comprising:
  at least one sensor configured to collect health data from a user,
  a controller configured to
   receive the health data collected by the at least one sensor, and
   determine a health parameter based on the health data, and
  a health monitoring device power supply configured to supply electrical power to at least one of the controller and the at least one sensor, the health monitoring device not being an aerosol generator for generating an aerosol from an aerosol-forming substrate;
 an aerosol-generating device comprising:
  a cavity configured to receive a plug of tobacco,
  an aerosol-generator configured to generate aerosol from the plug of tobacco, and
  an aerosol-generating device power supply configured to supply electrical power to the aerosol-generator,
  wherein the health monitoring device and the aerosol-generating device are separate devices; and
 a charging unit comprising:
  at least one cavity configured to receive the health monitoring device and the aerosol generating device, and
  a charging unit power supply,
 wherein the charging unit power supply is configured to transfer electrical power from the charging unit power supply to the health monitoring device power supply when the health monitoring device is received within the at least one cavity,
 wherein the charging unit power supply is further configured to transfer electrical power from the charging unit power supply to the aerosol-generating device power supply when the aerosol-generating device is received within the at least one cavity,
 wherein the at least one cavity is a single cavity configured to receive each of the health monitoring device and the aerosol-generating device,
 wherein the single cavity is sized to receive only one of the health monitoring device and the aerosol-generating device at a time,
 wherein the charging unit power supply is configured to transfer electrical power from the charging unit power supply to the health monitoring device power supply when the health monitoring device is received within the single cavity, and wherein the charging unit power supply is configured to transfer electrical power from the charging unit power supply to the aerosol-generating device power supply when the aerosol-generating device is received within the single cavity.

2. The aerosol-generating system according to claim 1, wherein the at least one sensor comprises at least one of an air flow sensor, an air pressure sensor, an audio sensor, and an electrochemical gas sensor.

3. The aerosol-generating system according to claim 2,
wherein the at least one sensor further comprises an electrochemical gas sensor, and
wherein the controller is further configured to determine at least one of breath carbon monoxide level and a breath nitrogen dioxide level based on the health data collected by the electrochemical gas sensor.

4. The aerosol-generating system according to claim 2, wherein the electrochemical gas sensor comprises a semiconductor gas sensor.

5. The aerosol-generating system according to claim 2,
wherein the at least one sensor further comprises at least one of an air flow sensor, an air pressure sensor, and an audio sensor, and
wherein the controller is further configured to determine a spirometry parameter based on the collected health data.

6. The aerosol-generating system according to claim 1, wherein the at least one sensor comprises at least one of an electrode, an optical sensor, and a pressure sensor.

7. The aerosol-generating system according to claim 6,
wherein the at least one sensor further comprises an optical sensor, and
wherein the controller is further configured to determine, based on the health data collected by the optical sensor, at least one of a heart rate, a heart rate variability, an oxygen saturation level, a carbon monoxide saturation level, and an oxidative stress level.

8. The aerosol-generating system according to claim 7,
wherein the optical sensor comprises a multiple spatially resolved reflection spectroscopy sensor, and
wherein the controller is further configured to determine an oxidative stress level based on the health data collected by the multiple spatially resolved reflection spectroscopy sensor.

9. The aerosol-generating system according to claim 7,
wherein the optical sensor further comprises at least one light emitting diode and at least one photodiode, and
wherein the controller is further configured to determine, based on the health data generated by the at least one photodiode, at least one of a heart rate, a heart rate variability, an oxygen saturation level, and a carbon monoxide saturation level.

10. The aerosol-generating system according to claim 6,
wherein the at least one sensor further comprises an optical sensor and a pressure sensor, and
wherein the controller is further configured to determine a blood pressure based on the health data generated by the optical sensor and the pressure sensor.

11. The aerosol-generating system according to claim 1,
wherein the health monitoring device further comprises a motion sensor, and
wherein the controller is further configured to
receive motion sensor data generated by the motion sensor, and
determine a motion parameter based on the motion sensor data.

* * * * *